United States Patent
Urano et al.

(10) Patent No.: US 8,936,550 B2
(45) Date of Patent: Jan. 20, 2015

(54) EYELIDS OPENING DEVICE WITH DRAPE

(75) Inventors: Toru Urano, Fukuoka (JP); Yukihiko Tamai, Nagano (JP)

(73) Assignees: Kurume University, Fukuoka (JP); Hakko Co., Ltd., Nagano (JP)

( * ) Notice: Subject to any disclaimer, the term of this patent is extended or adjusted under 35 U.S.C. 154(b) by 439 days.

(21) Appl. No.: 12/513,789

(22) PCT Filed: Nov. 6, 2007

(86) PCT No.: PCT/JP2007/071551
§ 371 (c)(1),
(2), (4) Date: Jun. 1, 2009

(87) PCT Pub. No.: WO2008/056662
PCT Pub. Date: May 15, 2008

(65) Prior Publication Data
US 2010/0041957 A1 Feb. 18, 2010

(30) Foreign Application Priority Data
Nov. 6, 2006 (JP) .................................. 2006-299823

(51) Int. Cl.
*A61B 1/32* (2006.01)
*A61B 17/02* (2006.01)

(52) U.S. Cl.
CPC ................................. *A61B 17/0231* (2013.01)
USPC ............................. 600/236; 600/206; 600/208

(58) Field of Classification Search
USPC ................................................ 600/184–236
See application file for complete search history.

(56) References Cited

U.S. PATENT DOCUMENTS 3,650,267 A * 3/1972 Anderson ...................... 128/853
4,412,532 A * 11/1983 Anthony ........................ 600/206
5,213,114 A * 5/1993 Bailey, Jr. ...................... 128/849

(Continued)

FOREIGN PATENT DOCUMENTS

JP            3062106       9/1999
JP          2005-512662     5/2005

(Continued)

OTHER PUBLICATIONS

Japanese Official Action dated Dec. 15, 2009 together with English language translation.
Extended European Search Report dated Jul. 18, 2014 from counterpart European patent Application No. EP 07831283.2.

*Primary Examiner* — Ellen C Hammond
(74) *Attorney, Agent, or Firm* — Scully, Scott, Murphy & Presser, PC

(57) ABSTRACT

An eyelids opening device with a drape comprising a flexible upper ring (1) applied in contact with the face while surrounding eyelids, a lower ring (2) inserted into a conjunctiva sac and applied in contact with the eyelids conjunctiva side, and an elastic sheet (3) of soft tubular thin film located to extend from the face side to the eyelids conjunctiva side and used to fix one end to the upper ring and to fix the other end to the lower ring by expanding, wherein the outside diameter at the smallest portion of the elastic sheet is substantially equal to or longer than the interpalpebral length (between upper and lower eyelids). Difference in size of conjunctiva sac or interpalpebral length of individuals is absorbed even by an appliance of one size, the eyelids can be opened by fitting the eyelids opening device to the eyelids or the face while burden on the eyeball is reduced and high safety is ensured.

15 Claims, 7 Drawing Sheets

(56) References Cited

U.S. PATENT DOCUMENTS

| | | |
|---|---|---|
| 5,433,190 A | 7/1995 | Sunalp |
| 5,632,284 A * | 5/1997 | Graether ............... 128/849 |
| 6,083,155 A | 7/2000 | Trese |
| 6,267,752 B1 | 7/2001 | Svetliza |
| 6,450,983 B1 | 9/2002 | Rambo |
| 6,675,805 B1 * | 1/2004 | Graether ............... 128/849 |
| 7,033,319 B2 * | 4/2006 | Pulford et al. ........... 600/208 |
| 7,087,050 B2 | 8/2006 | LaHaye |
| 7,175,594 B2 * | 2/2007 | Foulkes ............... 600/236 |
| 7,988,626 B2 * | 8/2011 | Horvath ............... 600/237 |
| 8,388,526 B2 * | 3/2013 | Ewers et al. ........... 600/208 |
| 2003/0176771 A1 * | 9/2003 | Pulford et al. ........... 600/208 |
| 2006/0102187 A1 * | 5/2006 | Mino Sotelo De Kaspar et al. ........... 128/849 |

FOREIGN PATENT DOCUMENTS

| | | |
|---|---|---|
| JP | 2005-515011 | 5/2005 |
| WO | WO 01/82799 A1 | 11/2001 |
| WO | WO 03/053229 A2 | 7/2003 |
| WO | WO 03/061480 A1 | 7/2003 |

* cited by examiner

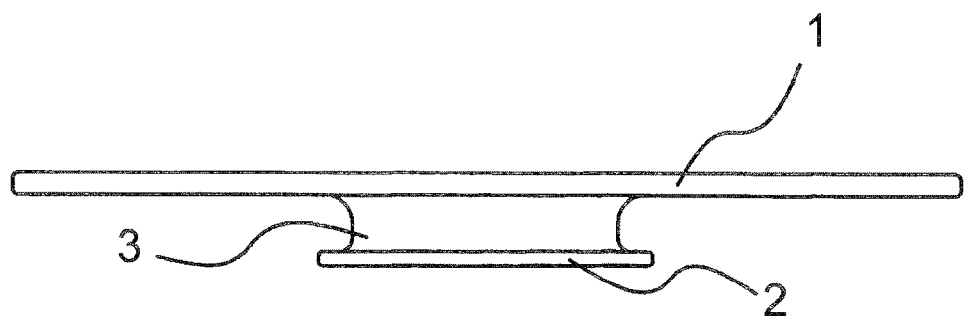
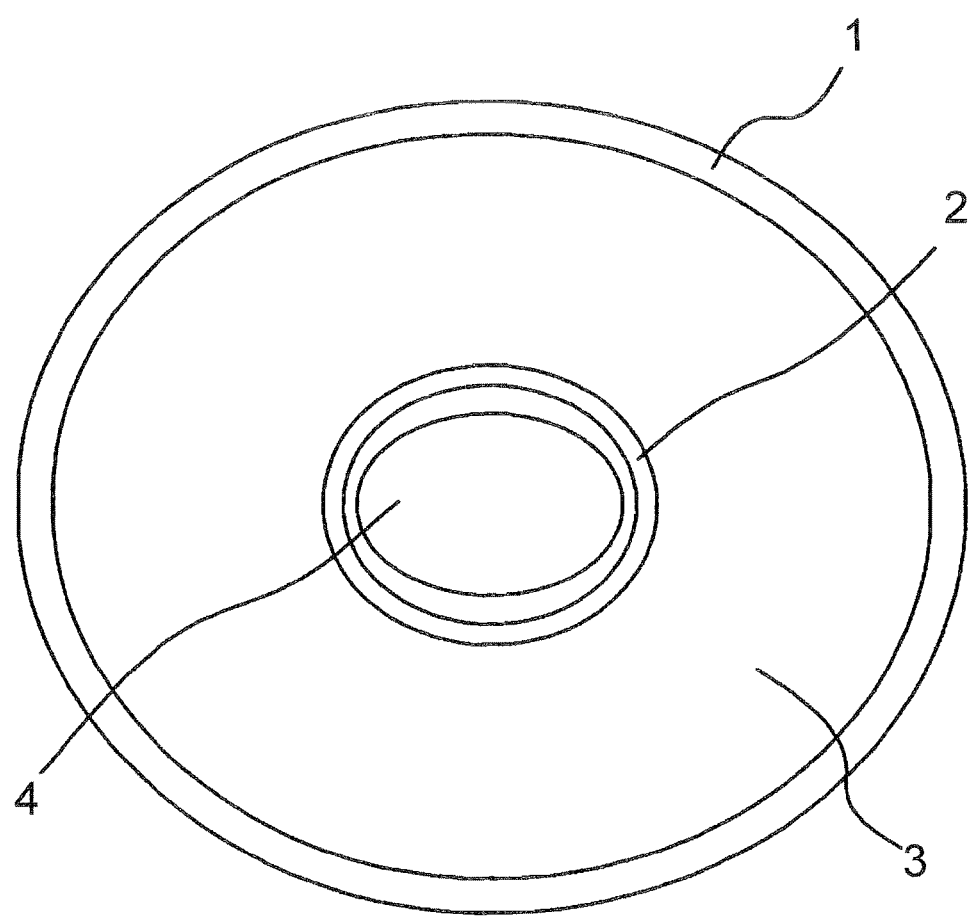

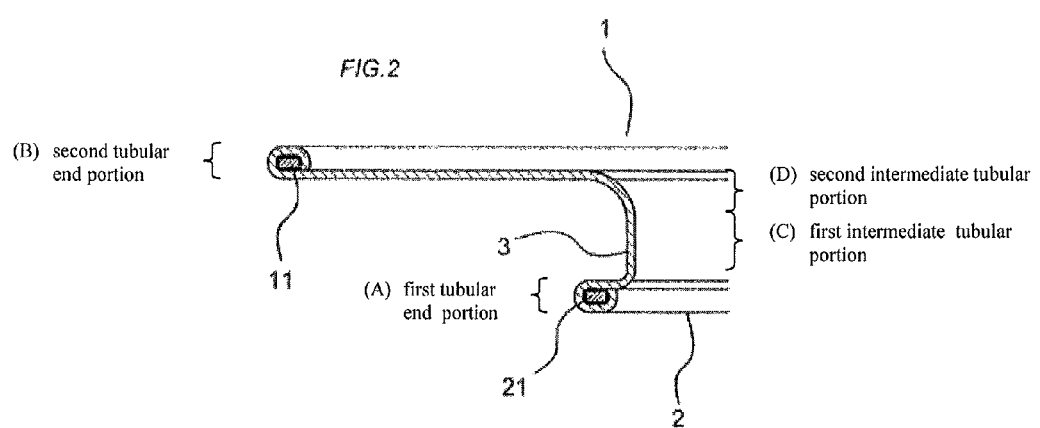

EYELIDS OPENING DEVICE WITH DRAPE

FIELD OF THE INVENTION

The present invention relates to an eyelids opening device for keeping an eyelid at an opened state, so as to prevent eyelashes or the like from exposing to an operative field for the purpose of the infection prevention and to keep a field of vision during an operation, at the time of an ophthalmic inner eye operation.

This application is based on Japanese Patent Application No. 2006-299823, and an entire contents of which is incorporated herein by reference.

RELATED ART

In ophthalmic operation or treatment to an eyeball, it is necessary to secure the enough operative field by keeping the eyelids at a forcibly opened state in upper and lower directions, so that an eyelids opening device is used as an device for this purpose. As conventional eyelids opening devices, a device for keeping the eyelids at a widely opened state by engaging hook portions such as metal fitting with an upper eyelid and a lower eyelid, thereby pulling the upper and lower eyelids in the upper and lower directions or the like has been generally known. Another proposed conventional eyelids opening device that is used by inserting a part thereof in a conjunctiva sac has a device with a flat cylindrical body as the whole, which comprises an aperture accessible to an eyeball, a waist part formed at a periphery of the aperture, a flared skirt part that is hung down from the waist part, in which the flared skirt part is formed as a flexible mold frame configured to be inserted into the conjunctiva sac to contact with and cover a part of the eyeball, and the waist part keeps the eyelids at the opened state (Patent document 1).

Patent document 1: JP-T 2005-512662

It is described that the eyelids opening device disclosed by the patent document 1 is advantageous in that a burden on the eyeball and a surrounding tissue is small, and that the drape for covering eyelashes and meibomian glands to prevent them from exposing to an operative field for the purpose of the infection prevention is needless, thereby facilitating an appliance of the eyelids opening device, compared with the conventional eyelids opening device in which the eyelids are hooked. However, since the size of the conjunctiva sac and a palpebral fissure are varied according to the age and the individual difference and so on, it is impossible to adapt such an eyelids opening device, which is formed as the mold frame to have a particular size, uniformly and widely applying to numerous individuals. Therefore, it is not beyond the realm of possibility that the fitting of this eyelid opening device may be uneasy appliance particularly for the person having a shallow conjunctiva sac or the person having a narrow palpebral fissure. In addition, since it is necessary to prepare the eyelids opening devices in plural sizes constantly for solving the above problem, this eyelids opening device is not necessarily convenient and easy applicable.

Furthermore, in the aforementioned device, the flared skirt part inserted in the conjunctiva sac is so thick and wide in area. Therefore, while a stable appliance during an operation can be provided, there is a concern that the impact on the eyeball may be increased due to an increase in contact area of the device with the eyeball, thereby affecting on the eyeball.

SUMMARY OF THE INVENTION

Accordingly, an object of the present invention is to provide an eyelids opening device with drape, that is an eyelids opening device to be used by inserting a part thereof in the conjunctiva sac, by which it is possible to keep eyelids at an opened state by fitting it to the eyelids, eyeball, and face surface, by widely and flexibly corresponding to a difference in size of the conjunctiva sac or interpalpebral length between individuals even in the appliance of the device in one size.

Further, another object of the present invention is to provide an eyelids opening device with drape, by which the burden on the eyelids, eyeball, or the like is reduced and high safety is ensured.

An eyelids opening device with a drape according to the present invention comprises:

a flexible upper ring to be applied in contact with a face while surrounding eyelids;

a lower ring to be inserted into a conjunctiva sac and applied in contact with an eyelids conjunctiva side; and an elastic sheet of a flexible tubular thin film located to extend from a face side to the eyelids conjunctiva side, the elastic sheet attaching one end to the upper ring and attaching the other end to the lower ring by expanding, respectively, wherein an outside diameter at a smallest portion of the elastic sheet is substantially equal to or greater than an interpalpebral length (between upper and lower eyelids).

In addition, it is preferable that respective parts have following structures or characteristics.

The upper ring and lower ring are formed in circular shape, elliptic shape, or quasi-elliptic shape. Herein, the "quasi-elliptic shape" means a shape which is beyond the realm of a definition of the elliptic, however, a general view of which as the whole is similar to the elliptic shape, e.g. a shape formed by compressing or pulling an elastic circular ring in two directions.

A maximum diameter part of the lower ring is formed in diameter or width from 25% to 40% of a maximum diameter part of the upper ring.

The elastic sheet comprises a transparent or translucent sheet.

The elastic sheet comprises a resin with a tensile elongation percentage of 600% or more.

Furthermore, it is more preferable that following structures or characteristics are added.

The lower ring is formed as a hollow structure comprising one or more through-holes, and provided with a tube forming a passage with a hollow inner part of the lower ring.

The upper ring or a part of an upper ring side of the elastic sheet is provided with a fixing means for attaching a tube. In addition, the fixing means may be such configured that the tube is detachable.

The elastic sheet is provided with one or more side-holes between the upper ring and the lower ring.

(Function)

According to the eyelids opening device with drape as described in the means for solving the problems, since the outer diameter of the smallest portion of the elastic sheet (a constricted part between the upper ring and the lower ring) is formed to be substantially equal to or greater than the interpalpebral length, and the elastic sheet is attached and fixed by expansion or the like to the upper ring and the lower ring, the palpebral fissure is pulled to an outer direction by means of a tension of the upper and lower rings and the elastic sheet, by inserting the lower ring of the eyelids opening device into the conjunctiva sac and applying it to the eyelids, thereby keeping the eyelids at the opened state while resisting against a closing force of the upper eyelid and the lower eyelid. Further, since the smallest portion of the elastic sheet is slightly compressed by the closing force of the upper eyelid and the lower eyelid, an interval between the upper ring located at a face side and the lower ring located at the eyelids conjunctiva side is narrowed. Therefore, a degree of close contact of the elastic sheet to inside and outside of the eyelids is increased, so that it is possible to hold the eyelids by sandwiching more securely. Further, a secure appliance state is naturally formed since the degree of close contact of the elastic sheet from a skin side to the eyelids conjunctiva side is increased.

Furthermore, since the upper ring has the flexibility, when the elastic sheet is compressed by the upper and lower eyelids as described above, the ring is pulled by the elastic sheet to be bent, so that the ring is naturally conformed to a face surface shape and closely applied to the face surface, thereby providing an appliance state in which the ring is further fitted to the face surface.

Still further, since the upper ring is formed in the elliptic shape or the quasi-elliptic shape, it is possible to apply the upper ring in conformity with the face surface without an instable appliance caused by sticking to the nose as a protrusion, while securing the size of the upper ring in a lateral direction of the face surface. On the other hand, it is possible to develop a wider field of vision in the lateral direction without changing a vertical length of the lower ring with respect to the eyeball, by forming the lower ring in the elliptic shape or the quasi-elliptic shape.

In addition, by forming the maximum diameter part of the lower ring in the length of 25% to 40% of the maximum diameter part of the upper ring, the upper ring will have dimensions for covering an appropriate area of the face surface when the lower ring is formed to have appropriate dimensions to be inserted into the eyeball, so that it is possible to provide the device that is most adapted to applications of the present invention. On the contrary, if a diameter of the lower ring is less than 25% of the upper ring, for example, it is highly probable that the upper ring may be so large that the upper ring would widely stick off the face surface when the lower ring is inserted into the eyeball. On the other hand, if the diameter of the lower ring is greater than 40% of the upper ring, it is highly probable that the upper ring would not cover the face surface enough when the lower ring is inserted into the eyeball.

Furthermore, since the elastic sheet is transparent or translucent, it is possible to give the treatment while confirming the states of the eyelids and the eyeball during the operation, so that it is possible to easily grasp an abnormal state such as bloodshot and drying, and to immediately cope with the abnormal state.

In addition, since the elastic sheet is formed to have the tensile elongation percentage of 600% or more, it is easy to attach the elastic sheet by expansion to the ring in a manufacturing process, and it is possible to achieve the effect caused by the elasticity after the appliance without any difficulty, thereby obtaining an appropriate opened state of the eyelids. On the contrary, if the tensile elongation percentage of the elastic sheet is less than 600%, for example, it will be difficult to carry out the manufacturing of the eyelids opening device by expanding the elastic sheet. In addition, it is concerned that the burden is applied on the eyelids because of an excessively opened state of the palpebral fissure due to an increase in the tension of the elastic sheet when applied to the inside of the conjunctiva sac. Further, it is concerned that a wrinkle occurs at the time of appliance due to a loss of the flexibility of the elastic sheet, so that it is difficult to securely provide the operative field.

In addition, in this eyelids opening device, a part of the elastic sheet which covers from the face surface (skin) side to the eyelids conjunctiva side undertakes a role as a drape, so that it is possible to prevent the infection caused by exposure of the eyelashes or a secretion from the meibomian glands without using an extra drape.

Furthermore, when the lower ring has the hollow structure comprising the through-holes, and is provided with the tube connecting with the lower ring as one of the devices in the present invention, it is possible to suck a water or secretion that is injected for preventing the eyeball from drying or for washing blood during the operation and collects in the operative part, through the tube. In addition, for example, it is possible to wash a deep part of the conjunctiva sac by refluxing the water from the tube, at the time of a continuous eye washing using a large quantity of physiological saline for treating alkaline chemical injuries.

Thereby, the upper ring or the elastic sheet is provided with the fixing means for attaching the tube, it is possible to suck the water or secretion collecting in the operative part through a suction tube by attaching the tube to the fixing means. Further, by forming the fixing means in which the tube is detachable, it is sufficient to attach the tube only when it is necessary. For example, if the tube is detached at the time of applying the device to the eyelids, the insertion will not be disturbed by the tube.

Further, when the elastic sheet is provided with the side-holes and an absorbent material (e.g. gauze, surgical cotton) is applied between a side hole part at an outer side of the elastic sheet and the conjunctiva sac, it is possible to absorb the water or secretion collecting in the operative part through the side-holes and drain it to the outside, by the capillary phenomena of the absorbent material.

(Advantages of the Invention)

According to the eyelids opening device with drape of the present invention, by the effect of the aforementioned structure and functions, it is possible to securely keeping the eyelids at the opened state and to securely apply the device to the eyelids. In addition, since the whole device is flexible except the lower ring, when this device is applied to the eyelids, a low-impact shape in conformity with the person to which the device is applied is naturally formed. Therefore, it is possible to hold the device while fitting to the eyelids and the face surface in the appliance of the device in one size, by widely corresponding to the individual difference.

Further, even when an area of the lower ring which is inserted into the conjunctiva sac and in contact with the eyelids conjunctiva side is reduced, it is possible to securely apply the device with holding the eyelids by sandwiching as described in the Function, so that it is possible to reduce the size of the lower ring compared with that of the conventional device. As a result, the contact area with the eyeball is reduced, thereby reducing the burden on the eyeball.

Furthermore, since the elastic sheet is transparent or translucent, it is possible to operate with confirming the state of the eyelids. Further, since the elastic sheet covers the eyelashes and the meibomian glands to prevent the exposure of the eyelashes or the meibomian glands to the operative field, it is possible to provide the device with high safety by which the prevention from the infection is expected.

In addition, by proving the means for draining the water or secretion colleting in the operative part, a drainage work for securing a clear operative field can be facilitated, thereby facilitating the operation.

BRIEF DESCRIPTION OF THE DRAWINGS

FIG. 1A is a front view of an eyelids opening device with drape in the first preferred embodiment according to the present invention;

FIG. 1B is a cross sectional view of the eyelids opening device with drape in the first preferred embodiment according to the present invention;

FIG. 2 is a partial cross sectional view of the eyelids opening device with drape in the first preferred embodiment according to the present invention;

EXPLANATION OF REFERENCE NUMERALS

Figure 3A:
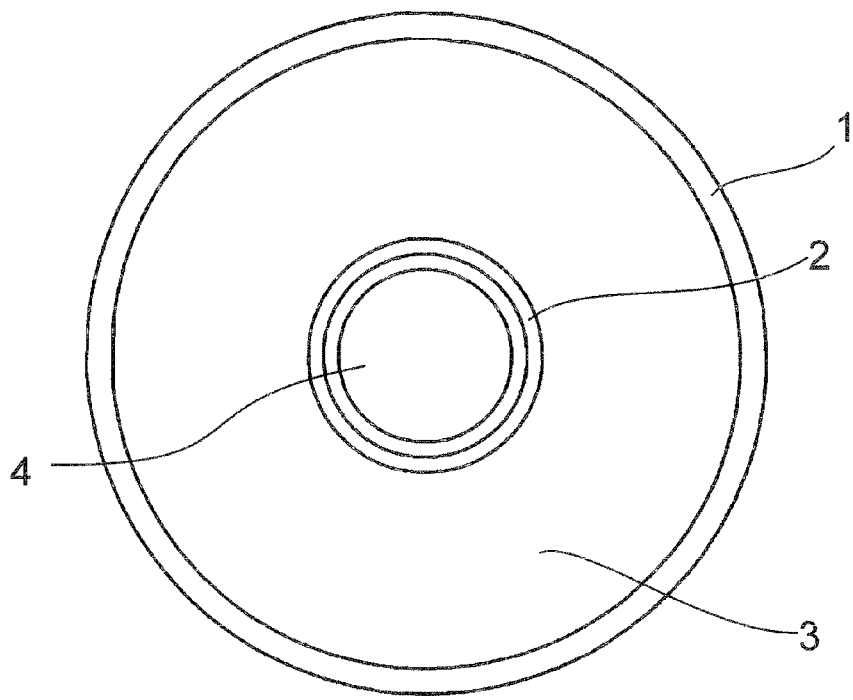
FIG. 3A is a bottom view showing a variation of the first preferred embodiment according to the present invention.

1 Upper ring
11 Upper plate
2 Lower ring
21 Lower plate
22 Hollow ring
23 Lumen
24 Through-hole
3 Elastic sheet
31 Hole
4 Aperture
5 Suction tube
51 Tube base
6 Fixing implement
61 Engaging portion (upper ring side)
62 Engaging portion (suction pipe side)
7 Suction pipe
71 Suction pipe base
8 Side-hole
9 Gauze

BEST MODE FOR CARRYING OUT THE INVENTION

Next, preferred embodiments of the present invention will be described in more detail in conjunction with appended drawings.

FIG. 1 is a total structural diagram of the eyelids opening device with drape in the first preferred embodiment according to the present invention, wherein FIG. 1A is a front view thereof, FIG. 1B is a bottom view thereof, and FIG. 2 shows a partial cross sectional view thereof.

The eyelids opening device with drape in this preferred embodiment comprises an upper ring 1 that is located at a face surface side, a lower ring 2 to be inserted into a conjunctiva sac (located at an eyelids conjunctiva side), in appliance to eyelids, and an elastic sheet 3 attached to the upper ring 1 and the lower ring 2 at both ends, that is located from the face surface side to the eyelids conjunctiva side, and also functions as a drape.

The upper ring 1 is formed by forming an upper plate 11 as a ring-shaped plate with a thin (around 0.6 mm to 1.2 mm, and 1.0 mm in the embodiment) and an elliptic shape or quasi-elliptic shape (hereinafter referred to as "elliptic shape") from a resin having a flexibility (Polyacetal resin in this embodiment), expanding one end of the elastic sheet 3 to be described later over the upper plate 11 to cover an entire periphery of the upper plate 11, and attaching it to the upper plate 11 by fusion or glueing, for the purpose of providing an operability for inserting the lower ring 2 into the conjunctiva sac (to be described later) or to provide a deformability for fitting with the face surface shape when applied to the eyelids. The size of the ring is not specified herein. However, the ring is formed to have a major axis of around 50 mm to 80 mm (68 mm in this embodiment) and a minor axis of around 45 mm to 75 mm (62 mm in this embodiment) in the ellipse, as the dimensions that satisfies a drape function in conformity with this application and is easily employed by fitting with the face surface, with considering the use of this device for a general adult. Further, a width of the upper plate 11 is around 1 mm to 3 mm (2.1 mm in this embodiment).

The lower ring 2 is formed by forming a lower plate 21 as a ring-shaped plate with a thin (around 0.5 mm to 1.0 mm, and 0.8 mm in the embodiment) and an elliptic shape from a relatively hard resin (Polyacetal resin in this embodiment), slightly expanding another end of the elastic sheet 3 over the lower plate 21, and attaching it to the lower plate 21 by fusion or glueing, similarly to the upper ring 1, with considering a stability in appliance of the lower ring 2 when inserted into the eyelids conjunctiva side (the conjunctiva sac). The size of the ring is not specified herein. However, the ring is formed to have a major axis of around 18 mm to 28 mm (24 mm in this embodiment) and a minor axis of around 15 mm to 26 mm (22 mm in this embodiment) in the ellipse, as the dimensions that enable a low-impact insertion into the conjunctiva sac, a development of the field of vision that is sufficient for the operation, and a stable holding in appliance, with considering the use of this device for a general adult. Further, a width of the lower plate 21 is around 0.8 mm to 1.5 mm (1.2 mm in this embodiment).

The elastic sheet 3 is formed as a tubular sheet comprising a translucent silicone resin that is flexible and provided with sufficient tensile elongation percentage (600% or more, 800% in this embodiment) as well as a thin film shape having a width of around 0.18 mm or more and 0.38 mm or less (0.25 mm in this embodiment). As described above, the elastic sheet 3 is configured to be attached to the upper plate 11 at one end and attached to the lower plate 21 at another end by expanding the respective ends, to provide an example of the eyelids opening device with drape of the present invention.

In addition, the shape of the tubular elastic sheet 3 before attaching to the upper and lower plates is not a specified herein. However, in this embodiment, a tubular sheet formed to have a large diameter at a side attached to the upper plate 11 and a small diameter at a side attached to the lower plate 21 is used, so as to facilitate the attachment to the plates at the time of manufacturing. Namely, a sheet having a lower half part formed to have a cylindrical shape with a small and constant diameter as the side attached to the lower plate 21, and an upper half part formed to have a diameter radially increased from the diameter of the lower part cylinder as the side attached to the upper plate 11 is used.

In addition, an inner diameter of the lower part cylinder is naturally equal to or greater than an interpalpebral length between the upper eyelid and the lower eyelid, and determined to be 20 mm as an appropriate length in this embodiment. Further, this size is also a size of an aperture 4 of the eyelids opening device without change.

Further, in this embodiment, the upper ring 1 and the lower ring 2 are formed to have the elliptic shape, so that the aperture 4 has an elliptic shape in coordination with the rings, even in a natural state where the aperture 4 is not applied to the eyelids. In addition, a length of the elastic sheet 3 between the upper ring 1 and the lower ring 2 that cooperatively hold the eyelids by sandwiching from inside and outside (a length of a gap between the upper ring and the lower ring) is determined to be around 2 mm or more and 6 mm or less (4 mm in this embodiment) in the natural state before attachment, as a length for holding securely and safely with a low-impact in the appliance.

Of course, the description (size and so forth) as described above is not specified herein, and it is sufficient to select the optimum size according to the object of the present invention. Further, since the transparency of the tubular sheet for forming the elastic sheet 3 is increased by reducing a thickness due to the expansion, the elastic sheet 3 is not necessarily transparent or translucent in the natural state (in the state before expansion) as long as the transparency after expansion can be surely provided.

Figure 3B:
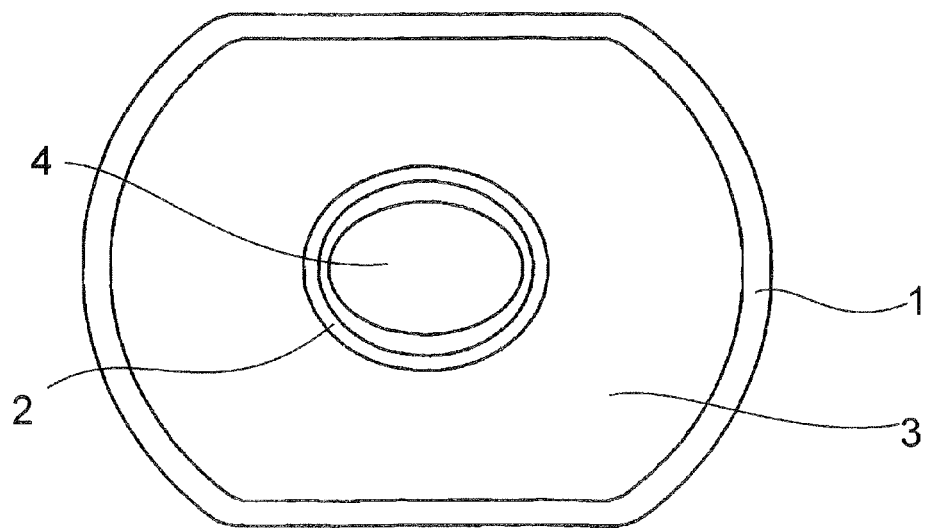
FIG. 3B is a bottom view showing another variation of the first preferred embodiment according to the present invention.

FIG. 3 is a bottom view of the eyelids opening device in the variation of the aforementioned preferred embodiment, which shows examples of the device in which the shape of the upper ring or the lower ring is not elliptical, wherein FIG. 3A shows a circular shape, and FIG. 3B shows a track-like shape as an example of the quasi-elliptic shape.

Figure 4A:
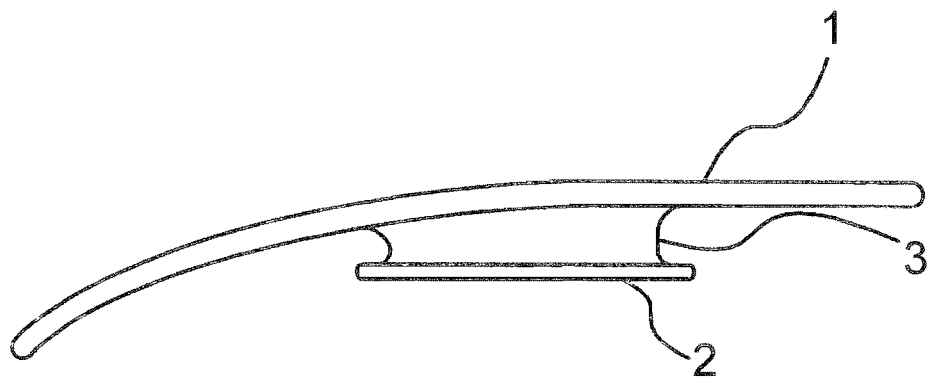
FIG. 4A is a front view of an eyelids opening device with drape in the second preferred embodiment according to the present invention.
Figure 4B:
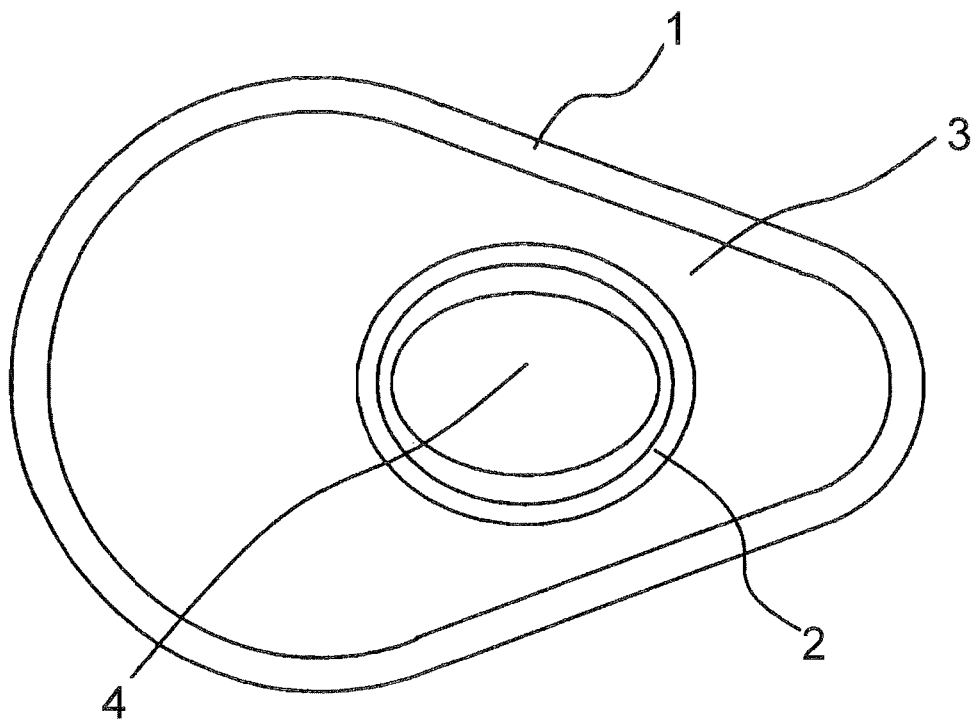
FIG. 4B is a cross sectional view of the eyelids opening device with drape in the second preferred embodiment according to the present invention.

FIG. 4 is a total structural diagram of the eyelids opening device with drape in the second preferred embodiment of the present invention, wherein FIG. 4A is a front view thereof, and FIG. 4B is a bottom view thereof.

In the eyelids opening device with drape in this embodiment, the shape of the upper ring 1 is previously formed to have a deformed droplet shape in place of the circular or elliptic shape so as to fit the face surface shape at an applied part more closely, and formed to be inclined to hang down from a nose side to an ear side in accordance with a curve of the face surface.

By using the upper ring 1 previously formed and having to have such a shape, it is possible to obtain a secure and close contact with the face surface when the device is applied to the eyelids, and it is possible to provide a shape which serves as an escape passage for the eye washing water at the time of the eye washing during the operation, so that the eye washing water hardly remains in the operative part.

As described above, the shape of the upper ring 1 is not limited to this embodiment (including the circular, elliptic shape and the like), and it is possible to adopt any appropriate shape with considering the face surface applied part.

Figure 5A:
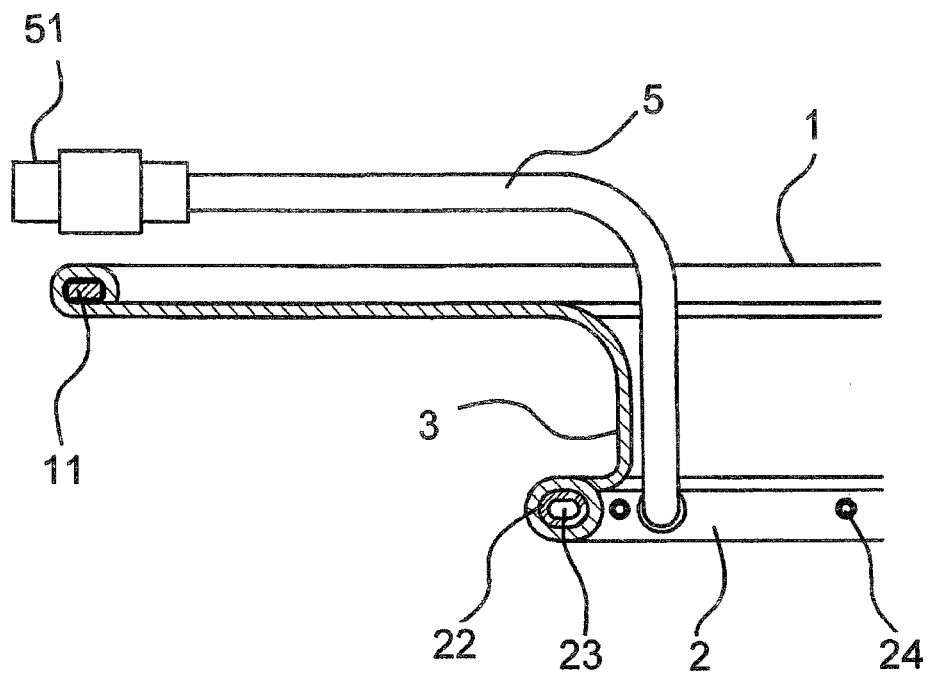
FIG. 5A is a schematic diagram of a partial cross section of an eyelids opening device with drape in the third preferred embodiment according to the present invention.
Figure 5B:
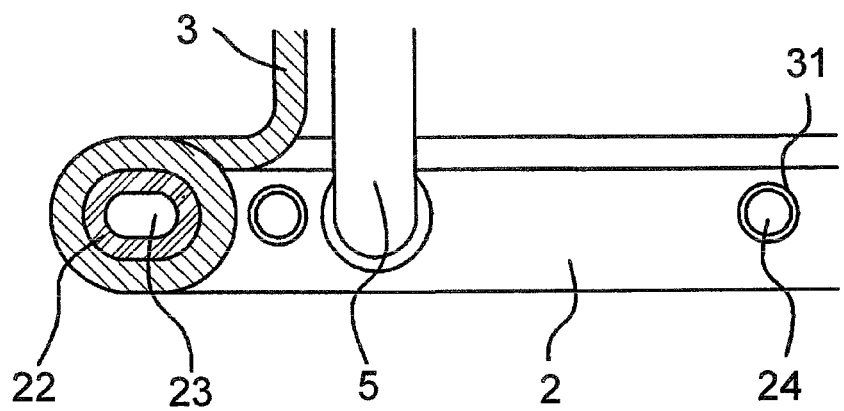
FIG. 5B is an enlarged view of an essential part of the eyelids opening device with drape shown in FIG. 5A.

FIG. 5 is a schematic diagram of a cross section showing the third preferred embodiment of the present invention, wherein FIG. 5B is an enlarged view of an essential part of FIG. 5A.

The eyelids opening device with drape in this embodiment comprises an upper ring 1 and an elastic sheet 3 that are similar to those in the first preferred embodiment, a lower ring 2 comprising a hollow structure provided with a plurality of through-holes 24, and a suction tube 5 which communicates with a hollow inner part (lumen) 23 of the lower ring via a passage that are original in this embodiment. Herein, since a total shape and size including the lower ring 2, or materials, characteristics or the like of the respective parts may be formed according to any device in the aforementioned preferred embodiments, they are not particularly described in this embodiment.

The lower ring 2 is formed by using a hollow ring 22 comprising a hollow structure in place of the lower plate 21 having the plate shape in the aforementioned embodiment, slightly expanding an end of the elastic sheet 3 over the hollow ring 22, and attaching it to the hollow ring 22 by adhesion or glueing. Further, the hollow ring 22 is provided with the through-holes 24 at a part which does not come into contact with the conjunctiva sac when inserted into the eyelids (a part located inside of the ring in this embodiment), and further, the elastic sheet 3 covering the hollow ring 22 is provided with a hole 31 that is greater than the through-hole 24 at a position corresponding to the through-hole 24, to provide a drain to the outside for the water or secretion that is injected for preventing the eyeball from drying or for washing the blood during the operation and collects in the operative part.

The suction tube 5 comprises a flexible resin (silicone resin in this embodiment) and formed to have a diameter as small as possible to the extent that a function of suction and the like is not affected, and one end thereof is connected to the hollow ring 22 while another end thereof is connected to a tube base 6 comprising a wide using tapered part that is located outside. The tube base 51, the suction tube 5, the hollow ring lumen 23, and the through-hole 24 (the hole 31 of the elastic sheet) are formed to provide a suction (injection) passage for the water or secretion.

According to the device in this embodiment, it is possible to suck and remove from the outside the water or the like that is injected to an eyeball surface during the operation and collects in the operative part when the lower ring 2 is applied to the conjunctiva sac, by using a suction pipe, suction device or the like via the lumen 23 of the hollow ring 22 and the tube 5.

Figure 6A:
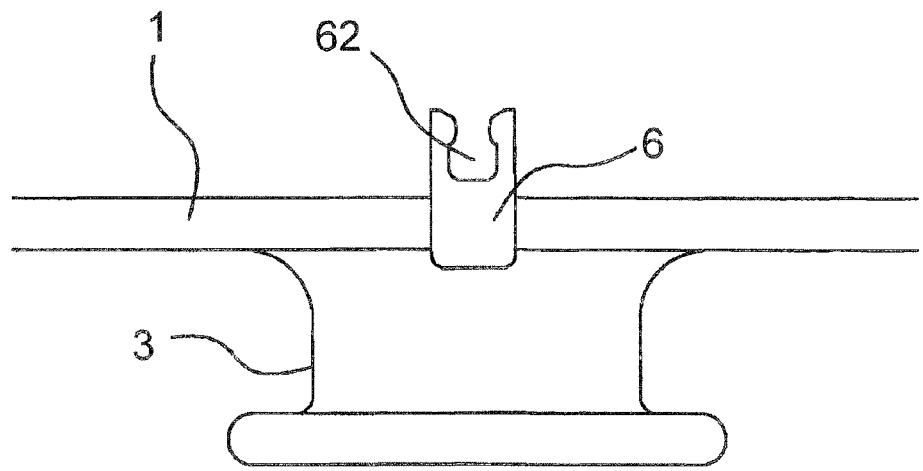
FIG. 6A is a partial front view of an eyelids opening device with drape in the fourth preferred embodiment according to the present invention, wherein a suction pipe is detached.
Figure 6B:
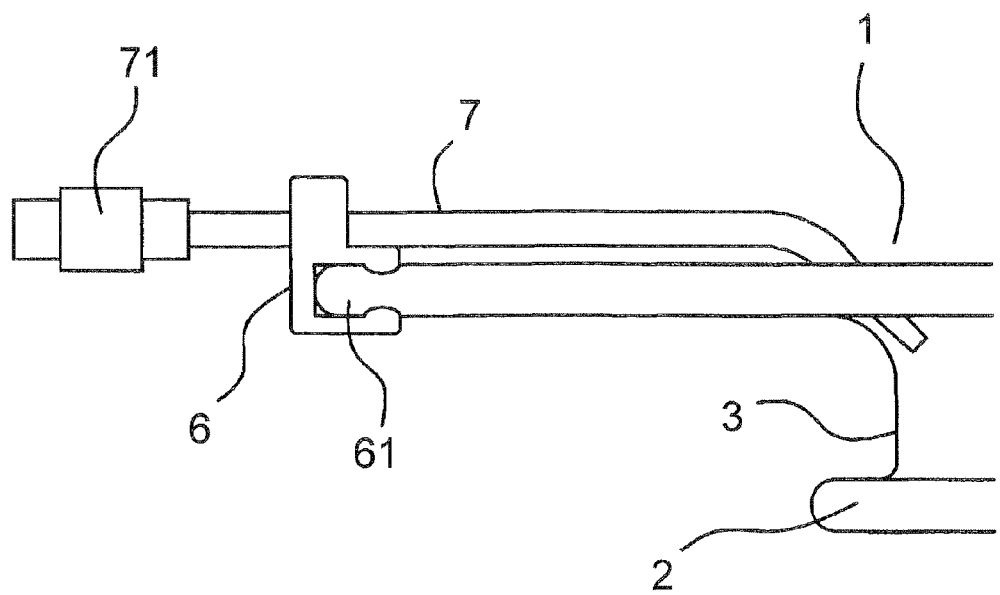
FIG. 6B is a partial front view of the eyelids opening device with drape in the fourth preferred embodiment according to the present invention, wherein the suction pipe is attached.

FIG. 6 is a schematic diagram showing a part of the fourth preferred embodiment according to the present invention, wherein FIG. 6A is a partial front view showing the state that a suction pipe is detached, and FIG. 6B is a partial front view showing the state that the suction pipe is attached.

The eyelids opening device with drape in this embodiment is configured to provide the upper ring 1 of the device in the first preferred embodiment with a fixing implement 6 for attaching a tube (suction pipe) 7 in freely detachable manner. Herein, since a total shape and size including the upper ring 1, or materials, characteristics or the like of the respective parts may be formed according to any device in the aforementioned preferred embodiments, they are not particularly described in this embodiment.

The fixing implement 6 is molded from a resin, and comprises an engaging portion 61 formed as a concave portion for fixing an appropriate position of the upper ring 1 by sandwiching from the upper and lower sides, and an engaging portion 62 formed as a concave portion for attaching a suction pipe 7 by sandwiching into both sides, and a tip portion of the concave portion in both of the engaging portion 61 and the engaging portion 62 is provided with a nail for securely fixing or attaching. The concave portion of the engaging portion 61 is formed to have a width slightly smaller than the thickness of the upper ring 1, and the concave portion is attached to the upper ring 1 by insertion such that the upper ring 1 is slightly compressed, thereby fixing the upper ring 1 by sandwiching between the upper and lower side. On the other hand, the concave portion of the engaging portion 62 is formed to have a width substantially equal to a diameter of the suction pipe 7, and the suction pipe 7 is fit into the concave portion by pressing, thereby holding the suction pipe by lightly sandwiching from the both sides, and easily detaching the suction pipe 7 by pulling out from the engaging portion 62.

The suction pipe 7 comprises a tube of resin or metal provided with a suction pipe base 71, a tip portion serving as a suction inlet is formed with a curve for bending to a lower side (an eyeball side) when the device is furnished to the eyelids.

According to the device in this embodiment, it is possible to suck from the outside the water or the like that is injected to the eyeball surface during the operation and collects in the operative part when the lower ring 2 is applied to the conjunctiva sac, by using a suction pipe, suction device or the like via the suction pipe 7. Further, it is possible to take off the suction pipe 7, when the suction pipe 7 is a hindrance to the work e.g. for attaching the device by insertion, since the suction pipe 7 is configured to be freely detachable.

Figure 7:
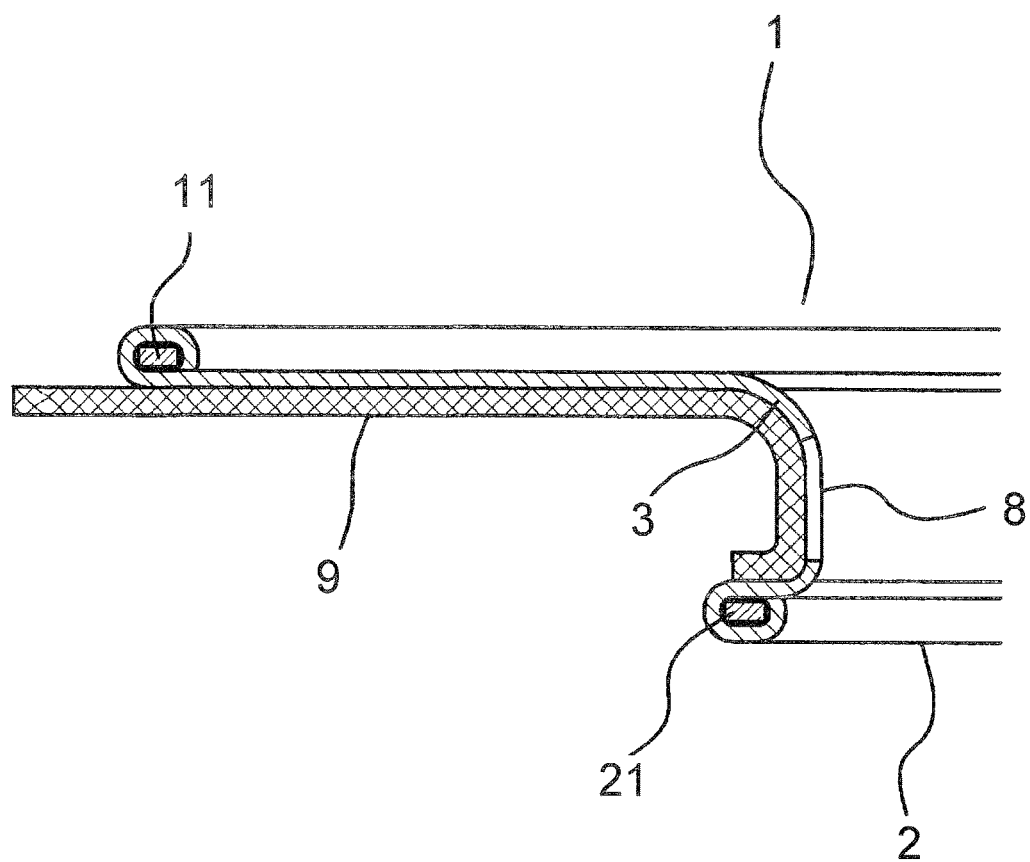
FIG. 7 is a schematic diagram of a partial cross section of an eyelids opening device with drape in the fourth preferred embodiment according to the present invention.

FIG. 7 is a schematic diagram of a cross section showing the fifth preferred embodiment of the present invention.

The eyelids opening device with drape in this embodiment comprises one or more side-holes 8 (a hole having a diameter of 2 mm provided at one location in this embodiment) provided at a part of an elastic sheet 3 between an upper ring 1 and a lower ring 2. Herein, since a total shape and size including the elastic sheet 3, or materials, characteristics or the like of the respective parts may be formed according to any device in the aforementioned preferred embodiments, they are not particularly described in this embodiment.

When this device is applied to the eyelids, a gauze 9 is disposed in practical use as an absorbent material in a gap between an outside of the side-hole 8 of the elastic sheet and a contact part with the conjunctiva sac.

According to the device in this embodiment, it is possible to absorb the water or the like that is injected to the eyeball surface during the operation and collects in the operative part when the lower ring 2 is applied to the conjunctiva sac by the gauze 9 through the side-hole 8, and to drain it to the outside by the capillary phenomena of the gauze 9.

In addition, the drainage from the side-hole 8 may be carried out by inserting a suction pipe as described above in place of the gauze 8 into the location for sucking the water or the like.

Next, as to the state of use in which the eyelids opening device with drape in this embodiment is applied to the eyelids, the function and the like will be again explained collectively.

The appliance of this device to the eyelids is carried out by widely opening the palpebral fissure, largely bending the upper ring 1 to be folded in half, simultaneously grasping a part of the lower ring 2 by fingers, and inserting the lower ring 2 from an opposite side with respect to the grasped side into the conjunctiva sac (the eyelids conjunctiva side).

After the lower ring 2 is inserted, the lower ring 2 is located to contact with the eyeball and the eyelids conjunctiva side, the upper ring 1 is located to contact with the face surface while surrounding the eyelids, and the elastic sheet 3 is located to contact from the skin side to the eyelids conjunctiva side. Further, maintaining in this state, the upper eyelid and the lower eyelid are opened by the elastic sheet 3 in the outer direction, so that the opened state of the eyelids is kept, then an aperture of the elastic sheet 3 is used as an aperture 4 for operation through which the operation is carried out.

Further, when the device is applied as described above, since the elastic sheet 3 is attached under expanded state to the upper ring 1 and the lower ring 2, the elastic sheet 3 keeps the eyelids at the opened state while resisting against the closing force of the upper eyelid and the lower eyelid. Simultaneously, the elastic sheet 3 is slightly compressed by the same closing force of the upper eyelid and the lower eyelid, so that the upper ring 1 and the lower ring 2 connected to the sheet are pulled in directions close to each other. Thus, a distance between the rings is shortened to some extent, so that a force for holding the eyelids by sandwiching by the upper ring 1 and the lower ring 2 is increased, then the eyelid is maintained in a stable appliance state. Further, since the upper ring 1 has the flexibility, a deformation such as bending is naturally occurred by the effect of this pulling, so that the degree of close contact with the face surface can be enhanced. Therefore, it is possible to obtain the appliance state adapted to the face surface shape (for example, a shape which is high at the nose side and inclined to the ear side).

In addition, the eyelids opening device of the present invention including all preferred embodiments as described above is expected to be a disposable (single-use) device, so that this device is cleaner, more convenient in use, and less complicated in use, compared with the conventional eyelids opening device that is used for plural times after general sterilization.

INDUSTRIAL APPLICABILITY

In addition, the present invention is not limited to operations of human being, but applied to operations of animal.

What is claimed is:

1. An eyelids opening device, comprising:
a flexible flat upper ring configured to be applied in contact with a face while surrounding upper and lower eyelids, the flexible upper ring having a flexibility to be foldable in half as well as a self-restoring property;
a flat lower ring configured to be inserted into a conjunctiva sac of the upper and lower eyelids; and
an elastic sheet of a flexible tubular thin film located to extend from a face side to the eyelids conjunctiva sac, one end of the elastic sheet having a large diameter expanded state at a side attached to the upper ring to form a drape and another end of the elastic sheet having a smaller diameter expanded state attached to the lower ring,
wherein an outside diameter at a smallest portion of the elastic sheet is substantially equal to or greater than an interpalpebral length between the upper and lower eyelids, and
wherein the expansion of the ends of the elastic sheet causes a corresponding tension in the upper and lower rings and the elastic sheet thereby maintaining the eyelids in an open state as a closing force of the upper and lower eyelids is resisted.

2. The eyelids opening device with drape according to claim 1, wherein the upper ring and lower ring are formed in circular shape, elliptic shape, or quasi-elliptic shape.

3. The eyelids opening device with drape according to claim 1, wherein a maximum diameter part of the lower ring is formed in length from 25% to 40% of a maximum diameter part of the upper ring.

4. The eyelids opening device with drape according to claim 1, wherein the elastic sheet is transparent or translucent.

5. The eyelids opening device with drape according to claim 1, wherein the elastic sheet comprises a resin with a tensile elongation percentage of 600% or more.

6. The eyelids opening device with drape according to claim 1, wherein the lower ring is formed as a hollow structure comprising one or more through-holes, and provided with a tube connecting with the lower ring.

7. The eyelids opening device with drape according to claim 1, wherein the upper ring or the elastic sheet is provided with a fixing means for attaching a tube.

8. The eyelids opening device with drape according to claim 7, wherein the fixing means is such configured that the tube is detachable.

9. The eyelids opening device with drape according to claim 1, wherein the elastic sheet is provided with one or more side-holes between the upper ring and the lower ring.

10. The eyelids opening device with drape according to claim 1, wherein the lower ring has a hardness greater than a hardness of the elastic sheet.

11. The eyelids opening device with drape according to claim 1, wherein an inner diameter of the upper ring is greater than an outer diameter of the lower ring.

12. The eyelids opening device with drape according to claim 1, wherein the upper ring has an elliptical shape with a major axis of 50 mm to 80 mm and a minor axis of 45 mm to 75 mm,
wherein the lower ring has an outer diameter smaller than an inner diameter of the upper ring.

13. An eyelids opening device, comprising:
a drape for surrounding upper and lower eyelids and covering a portion of a face, the drape comprising a first flat ring plate and a flat annular portion, one end of the flat annular portion having a large diameter expanded state at a side attached to the first flat ring plate;
a second flat ring plate to be inserted into a conjunctiva sac of the upper and lower eyelids; and
a tubular portion connecting the flat annular portion of the drape and the second flat ring plate;
wherein one end of the tubular portion has a smaller diameter expanded state at a side attached to the second flat ring,
wherein the drape folds in half when bent and restores by itself when released,
wherein the annular portion and the tubular portion comprises the same elastic sheet and are formed continuously,
wherein an outside diameter of a smallest portion of the tubular portion is substantially equal to or greater than an interpalpebral length between the upper and lower eyelids, and
wherein an outside diameter of the second flat ring plate is greater than the outside diameter of the tubular portion and smaller than the outside diameter of the first flat ring plate.

14. The eyelids opening device with drape according to claim 13, wherein the first flat ring has an elliptical shape with a major axis of 50 mm to 80 mm.

15. An eyelids opening device comprising:
a first ring plate configured to be inserted into a conjunctiva sac of an upper eyelid and a lower eyelid, wherein the first ring plate has a first flexibility;
a second ring plate spaced apart from the first ring plate, wherein the second ring plate has a second flexibility greater than the first flexibility; and
a tubular sheet of flexible elastic film, the tubular sheet comprising:
a first tubular end portion defining a first opening of the tubular sheet, wherein the first tubular end portion is attached to the first ring plate;
a second tubular end portion defining a second opening of the tubular sheet, wherein the second tubular end portion is attached to the second ring plate;
a first intermediate tubular portion provided closer to the first tubular end portion than the second tubular end portion, and
a second intermediate tubular portion extending from the first tubular intermediate portion toward the second tubular end portion,
wherein the first intermediate tubular portion is configured to elastically maintain a substantially constant first diameter, and the second intermediate tubular portion is configured to elastically maintain a variable second diameter that radially increases from the first diameter as the second intermediate tubular portion extends toward the second tubular end portion.

* * * * *